US010314879B2

(12) United States Patent
McInnes

(10) Patent No.: US 10,314,879 B2
(45) Date of Patent: Jun. 11, 2019

(54) HONEY COMPOSITION WITH L-ALANYL-L-GLUTAMINE

(75) Inventor: Mike McInnes, Edinburgh (GB)

(73) Assignee: Benenox Limited, Edinburgh (GB)

( * ) Notice: Subject to any disclaimer, the term of this patent is extended or adjusted under 35 U.S.C. 154(b) by 215 days.

(21) Appl. No.: 14/114,649

(22) PCT Filed: May 16, 2012

(86) PCT No.: PCT/GB2012/051090
§ 371 (c)(1),
(2), (4) Date: Jan. 13, 2014

(87) PCT Pub. No.: WO2012/156731
PCT Pub. Date: Nov. 22, 2012

(65) Prior Publication Data
US 2014/0186457 A1 Jul. 3, 2014

(30) Foreign Application Priority Data
May 18, 2011 (GB) .................... 1108343.3

(51) Int. Cl.
A61K 38/05 (2006.01)
A61K 35/644 (2015.01)

(52) U.S. Cl.
CPC ............ *A61K 38/05* (2013.01); *A61K 35/644* (2013.01)

(58) Field of Classification Search
None
See application file for complete search history.

(56) References Cited

U.S. PATENT DOCUMENTS

| | | | | |
|---|---|---|---|---|
| 4,532,143 A * | 7/1985 | Brain | ............ | A23L 1/0524 426/577 |
| 4,973,491 A * | 11/1990 | Shin | ............ | A23L 1/08 426/632 |
| 2010/0168040 A1* | 7/2010 | Komatsu | ............ | A23L 1/3053 514/20.7 |
| 2010/0197787 A1* | 8/2010 | Doi et al. | ............ | 514/561 |
| 2010/0234308 A1 | 9/2010 | Komatsu | | |

FOREIGN PATENT DOCUMENTS

| | | |
|---|---|---|
| CN | 101041008 A | 9/2007 |
| CN | 101287458 | 10/2008 |
| CN | 101999572 A | 4/2011 |
| DE | 2919059 | 11/1980 |
| DE | 2919059.8 A1 | 11/1980 |
| JP | H04234959 A | 8/1992 |
| JP | H05213747 A | 8/1993 |
| JP | 2009256357 A | 11/2009 |
| WO | 2007/119503 A1 | 10/2007 |
| WO | 2010043486 A1 | 4/2010 |

OTHER PUBLICATIONS

Bogdanov et al., Honey for Nutritiona nd health: A Review, 2008, J American College Nutrition, 27: 677-689.*
International Search Report and Written Opinion issued in International Application No. PCT/GB2012/051090 dated Sep. 5, 2012.
Fessenden, R., "Honey—More than Just a Sweetner, Naturally", AAS Journal, Sep. 2007, 4 pages.
Lingling Yan et al. "Chemical component and pharmacological effects of honey", Special Economic Animal and Plant vol. 2, 2005—pp. 40 and 42.
Office Action from Corresponding Japanese Patent Application No. 2014-510877 dated Nov. 10, 2015.
Kreider, R. et al, "Honey: An Alternative Sports Gel", Strength and Conditioning Journal, Feb. 2002, 3 pages.
Ziegler, T., "Glutamine Supplementation in Cancer Patients Receiving Bone Marrow Transplantation and High Dose Chemotherapy", Journal of Nutrition, 2001, 7 pages.
Furst, P., "New Developments in Glutamine Delivery", Journal of Nutrition, 2001, 7 pages.
Notification of Reasons for Refusal for 2016-210960, dated Aug. 15, 2017, as issued by the Japanese Patent Office.
Official Decision of Refusal for 2014-510877, dated Jun. 28, 2016, as issued by the Japanese Patent Office.
David W. Ball, "The Chemical Composition of Honey," J. Chem. Educat. 84(10):1643-1646 (2007).
Sustamine® product description; https://kyowa-usa.com/branded-ingredients/sustamine-l-alanyl-l-glutamine (last accessed Dec. 27, 2017).
Examination Report, issued in corresponding in Patent Application No. 10751/DELNP/2013, dated Sep. 27, 2018.

* cited by examiner

*Primary Examiner* — Terry A McKelvey
*Assistant Examiner* — Catheryne Chen
(74) *Attorney, Agent, or Firm* — Brinks Gilson & Lione

(57) ABSTRACT

The present invention relates to compositions includes honey and L-alanyl-L-glutamine, pharmaceutical compositions thereof and a combined product comprising honey and L-alanyl-L-glutamine for a simultaneous, separate or sequential use in therapy. The composition, pharmaceutical composition and combined product have particular utility in improving sleep and treating sleep disorders such as insomnia or sleep apnoea.

24 Claims, No Drawings

HONEY COMPOSITION WITH L-ALANYL-L-GLUTAMINE

This is a 371 of PCT/GB2012/051090, which claims priority from GB 1108343.3, which is incorporated herein by reference in its entirety.

The present invention relates to compositions that include honey and L-alanyl-L-glutamine. The invention further relates to compositions, pharmaceutical compositions and combined products that have a therapeutic utility.

For humans to survive the following fundamental conditions must be met: adequate shelter/warmth/clothing/sufficient food/nutritive energy, and around 8 hours of recovery sleep during the dark phase of the light/dark cycle. In modern western metropolitan humans the first two of these are usually met, but the third is not, and increasingly less so. According to the National Sleep Foundation of the USA, Americans are sleeping up to two hours less than is required. Furthermore the relation between nutritive energy and sleep is perhaps the most neglected area of research in all of the life sciences, and that neglect is most expressed with respect to the relation between cerebral energy provision, and the duration and quality of sleep.

There are a large number of hypnotic or soporific drugs available today that assist with sleep and the treatment of sleep disorders; for example, benzodiazepines. Drug induced sleep is however often reported to induce a sleep that is not fully refreshing and includes a number of adverse effects (e.g. induction of dependency).

More natural remedies for sleep are therefore often preferred.

Honey is a natural sweet product made by bees. For thousands of years honey has been suggested for use in a wide variety of therapeutic applications. Honey is known to have antimicrobial and cough suppressant qualities. For many years it has been believed that honey can be taken in order to improve sleep. Recent studies have validated this belief.

There remains however a need to provide a honey based composition for improving sleep or treating sleep disorders that is more efficient than honey alone.

Surprisingly, the applicant has identified that one can improve sleep through the administration of honey and L-alanyl-L-glutamine.

Accordingly, in a first aspect of the present invention there is provided a composition comprising honey and L-alanyl-L-glutamine.

The honey and L-alanyl-L-glutamine are provided in the composition in a therapeutically effective amount thereof. Optionally, the L-alanyl-L-glutamine is no more than 10% or 6% by weight of the total composition. The composition may include from 0.5 to 10%, 1% to 10%, 0.5 to 6%, or from 2% to 6%, by weight L-alanyl-L-glutamine.

The composition may include 90% or 94% by weight honey, or more. The composition may include from 90% to 99.95, from 90 to 99.9%, from 90 to 99%, 98% to 99.95, from 98 to 99.9%, from 98 to 99%, or from 98% to 94%, honey by weight.

The composition may comprise or consist of 50 grams honey and 0.5 grams of L-Alanyl-L Glutamine.

The composition may include a number of additional components. However, the composition may consist essentially of honey and L-alanyl-L-glutamine.

Optionally, the only amino acids in the composition are dipeptides or polypeptides. Although, amino acid monomers may be present in the honey.

Optionally, the composition does not include any one or all of L-isoleucine, L-leucine and L-valine.

Optionally, the only source of carbohydrate in the composition is from honey.

Optionally, the only source of glucose in the composition is from honey.

Optionally, the composition may further comprise a solvent such as water. The water may be heated, in order to assist in the dissolution of the honey. In embodiments of the present invention where water is included, the preferred proportion of the compositions that are derived from L-alanyl-L-glutamine and/or honey, as expressed above, are expressed as percentage by weight in the absence of the water.

As the composition according to the first aspect of the present invention has utility in a therapeutic application, a second aspect of the present invention provides a pharmaceutical composition comprising a composition of the first aspect of the present invention and one or more pharmaceutically acceptable diluent, excipient or carrier. The pharmaceutical composition of the second aspect of the present invention may include any one or more feature described above in relation to the first aspect of the present invention.

As a pharmaceutical composition, the composition preferably is not prepared as a food-replacement or as a dietary supplement in food or beverages.

A further aspect of the present invention is a method for improving sleep or for treating sleep disorders (optionally insomnia or sleep apnoea), wherein the method includes the step of administering the composition, pharmaceutical composition, or combined product, to a subject in a therapeutically effective amount.

The composition may be administered orally, optionally in liquid form. The composition may therefore be prepared by being dissolved in a solvent (optionally water, which may be hot water).

Furthermore, in a fourth aspect of the present invention there is provided a combined product comprising honey and L-alanyl-L-glutamine for simultaneous, separate or sequential use in therapy.

The combined product of the fourth aspect of the present invention may include any one or more features of the first or second aspect of the present invention.

For example, 10% or 6% of the combined weight of honey and L-alanyl-L-glutamine of the combined product may be L-alanyl-L-glutamine, or less. From 0.5 to 10%, 1% to 10%, 0.5 to 6%, or from 2% to 6%, of the combined weight of honey and L-alanyl-glutamine may be L-alanyl-L-glutamine.

Optionally, 90% or 94% of the combined weight of honey and L-alanyl-L-glutamine is honey, or more. In a further embodiment, from 90% to 99.95, from 90 to 99.9%, from 90 to 99%, 98% to 99.95, from 98 to 99.9%, from 98 to 99%, or from 98% to 94%, of the combined weight of honey and L-alanyl L-glutamine may be honey. The combined product may comprise or consist of 50 grams honey and 0.5 grams of L-alanyl-L Glutamine.

The combined product may be prepared as a composition comprising honey and L-alanyl-L-glutamine.

The combined product of the fourth aspect of the present invention may include any one or more of the features described above in relation to the first or second aspect of the present invention.

The combined product may be used in a method for improving sleep. An improvement in sleep may be characterised as an improvement in the quality of sleep (ie the feeling of refreshment following sleep), the duration of sleep, a decrease in the period required to attempt to induce sleep, state on waking from sleep, or a combination of the above. In a further embodiment of the present invention the combined product may be used in a method for treating sleep disorders (e.g. insomnia or sleep apnoea).

The combined product, composition, or pharmaceutical composition of the present invention is preferably administered shortly before the recipient wishes to induce sleep. Preferably, the composition is taken within one hour, 45 minutes, 30 minutes, 15 minutes or 10 minutes prior to the time the recipient wishes to induce sleep. In one embodiment, the recipient is administered the combined product immediately prior to retiring to bed.

The combined product may be prepared for oral or rectal administration.

These and other aspects of the invention will now be described by way of example only.

Honey is a natural sweet product made by bees after being fed with nectar or other plant secretions obtained directly from a flower or plant, enzymes produced by the bees are added to that nectar or other secretions to produce honey. Preferably, the honey is produced by bees of the species *Apis meliferra*. The honey is preferably whole honey and not any extract or reduction therefrom.

L-alanyl-L-glutamine is a dipeptide of the following structural formula.

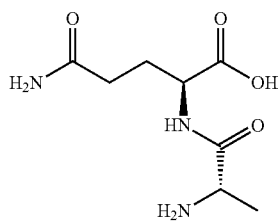

The term L-alanyl-L-glutamine includes pharmaceutically acceptable salts thereof.

The composition, pharmaceutical composition or combined product according to the present invention may be prepared by combining honey and L-alanyl-L-glutamine in a 3 to 47 ratio by weight. Water may be added. The composition is then drunk by an individual shortly before retiring to bed.

Not wishing to be restricted further but in the interest of clarity, the inventors theorise that it is the present inventions ability to provide a good energy source during sleep that provides the aforementioned benefits. In human sleep during the dark phase of the light/dark cycle, the brain is tasked with two vital considerations, that of optimising recovery physiology, and processing short term memories (hippocampus) into long term (neocortex) during REM sleep. Each of these two vital physiologic activities is absolutely dependent on optimal provision of cerebral energy over the hours of the nocturnal fast, and this provision presents the brain with a major metabolic challenge, if the hypothalamus/pituitary/adrenal (HPA) axis is not to be chronically stimulated. The human brain is the highest regulatory authority in the human organism, and this applies to all systems of metabolism and physiology, and above all to the acquisition, regulation and allocation of energy resources, since this organ has on the one hand, the highest energy demand, and on the other, very low energy storage capacity. In periods when energy resources are at a premium (sleep/exercise) the brain is forced to compete for energy with all other organs and tissues, with the overriding proviso that its needs are given absolute priority, over and above that of all peripheral organs. During the hours of the nocturnal fast, it is theorised that the brain relies almost exclusively on liver glycogen to provide reserve energy supply. The two systems available to the brain to optimise its energy supply are food ingestion and stress physiology. Since food is not normally ingested during the hours of the nocturnal fast, if the liver is not optimally provisioned prior to sleep, the brain is obliged to activate the HPA system as the only means of expropriating energy from the body (periphery) in favour of cerebral energy provision (The Selfish Brain Theory). Cerebral energy is indexed at 4 levels. Neural ATP, astroglial glycogen, blood glucose concentration, and liver glycogen. The first two would provision energy for less than a minute, the third significantly less than an hour in the absence of replenishment, and therefore the critical nocturnal cerebral energy reserve is liver glycogen, as indexed by the liver stress signal, IGFBP-1. In healthy humans the liver glycogen status signal IGFBP-1, denoting depleting liver glycogen reserve, rises by a factor of 4 from a 6 pm meal. This increase in IGFBP-1 results in inhibition of IGF-1 the key recovery physiology hormone, along with activation of the HPA axis, the only method that the brain may use to increase liver glycogen plenitude.

It is theorised that the present invention preferentially increases liver glycogen stores in advance of sleep.

A study has been prepared in order to demonstrate the effect of the consumption of the composition of the present invention on sleep.

1. Preparation of a Single Dose Composition (Hibernation Honey)

50 grams honey and 0.5 grams of L-Alanyl-L Glutamine were mixed in a plastic vial, prior to the mixture being poured into a drinking vessel and dissolved in hot water. Any residue of the mixture in the vial was mixed with hot water and poured into the drinking vessel and stirred; so as to ensure that all the honey and di-peptide ended up in the drinking vessel. In this way a single dose composition is prepared in the drinking vessel. The honey used was a blended honey (Tesco standard blend). The L-Alanyl-L Glutamine (®Sustamine) used was obtained from Kyowa International via Infra Foodbrands, a Dutch Beverage company.

2. Analysis of Composition on Sleep

Analysis of the effect of Hibernation Honey on sleep for 7 healthy adults between the ages of 25 and 75 was carried out over a continuous 6-day period.

During a first 3-day period (days 1 to 3), during which there was no consumption of Hibernation Honey, the sleep onset latency, sleep quality, sleep duration, dream recall and morning sickness was measured for each night of the 3-day period for each of the 7 adults.

Over the following 3 days (days 4 to 6), the same adults consumed a single dose of the Hibernation Honey (as described above) in the last half hour prior to going to bed. Measurements were taken for sleep onset latency, sleep quality, sleep duration, dream recall and morning sickness for each night of the 3 days (days 4 to 6) for each of the 7 adults.

The subjects were asked to record the time they went to bed and the time they woke from sleep. The following morning, shortly after waking and based on the recorded times and their memory of events, each subject was required to estimate the time for sleep onset and sleep duration. Sleep quality was measured by asking the adults to record their sleep quality each morning, shortly after waking during each morning of the study, as one of the following four categories: Very Poor/Poor/Adequate/Good. The adults were additionally asked to record dream recollection and any feelings of nausea shortly after waking during each morning of the study.

3. Results

Sleep Onset Latency:

On days 1-3 the total time of the 7 subjects was: 552 minutes.

On days 4-6 the total time of the 7 subjects was: 468 minutes—a reduction of 15.2%

Sleep Duration:

On days 1-3 the total time of sleep duration for the 7 subjects was: 140.75 hours On days 4-6 the total time of sleep duration for the 7 subjects was: 152 hours—an increase of 7.9%.

Sleep Quality:

On days 1-3 the 7 respondents recorded sleep quality as 2 Poor//12 Adequate//7 Good.

On days 4-6 the 7 respondents recorded sleep quality as 1 Poor//7 Adequate//13 Good—a clear trend to improved quality.

Dream Recall—no significant results.

Morning Sickness—no significant results.

Conclusion:—Hibernation Honey taken in the half hour prior to bedtime reduced sleep onset latency, and improves sleep duration and quality.

The invention claimed is:

1. A composition for improving sleep more efficiently than honey alone comprising honey in an effective amount to improve sleep in a subject in need thereof and 1% to 10% by weight of the composition of L-alanyl-L-glutamine or pharmaceutically acceptable salts thereof.

2. The composition of claim 1, further comprising a solvent.

3. The composition of claim 1, further comprising one or more pharmaceutically acceptable diluents, excipients, or carriers.

4. A combined product for improving sleep more efficiently than honey alone comprising honey in an effective amount to improve sleep in a subject in need thereof and 1% to 10% by weight of the composition of L-alanyl-L-glutamine or pharmaceutically acceptable salts thereof for simultaneous, separate, or sequential administration in sleep therapy.

5. The combined product of claim 4, wherein the composition consists essentially of honey and L-alanyl-L-glutamine.

6. The composition of claim 1, for use in the treatment of insomnia.

7. The composition of claim 1, for use in treatment of sleep apnoea.

8. The combined product of claim 4, for use in a method of improving sleep comprising the step of administering the combined product to the subject to be treated within 30 minutes prior to sleep.

9. The combined product of claim 6, for use in a method of treating insomnia comprising the step of administering the composition to the subject to be treated within 30 minutes prior to sleep.

10. The composition of claim 7, for use in a method of treating sleep apnoea comprising the step of administering the composition to the subject to be treated within 30 minutes prior to sleep.

11. The combined product of claim 4, wherein the honey and L-alanyl-L-glutamine are prepared as a single composition.

12. A method for treating a sleep disorder by administering to a subject suffering from the sleep disorder the composition of claim 1.

13. The method of claim 12, wherein the sleep disorder is insomnia.

14. The method of claim 12, wherein the sleep disorder is sleep apnoea.

15. The method of claim 12, wherein the honey and L-alanyl-L-glutamine are administered as a composition consisting essentially of honey and L-alanyl-L-glutamine.

16. The method of claim 12, wherein the honey and L-alanyl-L-glutamine are administered as a combined product comprising honey and L-alanyl-L-glutamine for simultaneous, separate, or sequential administration in sleep therapy.

17. The method of claim 16, wherein the combined product consists essentially of honey and L-alanyl-L-glutamine.

18. The method of claim 12, comprising the step of administering the honey and L-alanyl-L-glutamine to the subject to be treated within 30 minutes prior to sleep.

19. A method of improving sleep comprising administering to a subject in need of improved sleep the composition of claim 1.

20. The method of claim 19, wherein the honey and L-alanyl-L-glutamine are administered as a composition consisting essentially of honey and L-alanyl-L-glutamine.

21. The method of claim 19, wherein the honey and L-alanyl-L-glutamine are administered as a combined product comprising honey and L-alanyl-L-glutamine for simultaneous, separate, or sequential administration in sleep therapy.

22. The method of claim 21, wherein the composition consists essentially of honey and L-alanyl-L-glutamine.

23. The method of claim 19, comprising the step of administering the composition to the subject to be treated within 30 minutes prior to sleep.

24. A composition for improving sleep more efficiently than honey alone comprising honey in a therapeutically effective amount to improve sleep in a subject in need thereof and 1% to 10% by weight of the composition of L-alanyl-L-glutamine or pharmaceutically acceptable salts thereof, and one or more pharmaceutically acceptable diluents, excipients, or carriers.

* * * * *